(12) United States Patent
Granegger et al.

(10) Patent No.: US 11,067,085 B2
(45) Date of Patent: Jul. 20, 2021

(54) METHOD FOR DETERMINING OPERATIONAL PARAMETERS OF A BLOOD PUMP

(71) Applicant: Berlin Heart GmbH, Berlin (DE)

(72) Inventors: Marcus Granegger, Perchtoldsdorf (AT); Robert Steingräber, Berlin (DE); Jonas Fabian Krone, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 199 days.

(21) Appl. No.: 16/312,817

(22) PCT Filed: Jun. 29, 2017

(86) PCT No.: PCT/EP2017/066214
§ 371 (c)(1),
(2) Date: Dec. 21, 2018

(87) PCT Pub. No.: WO2018/002271
PCT Pub. Date: Jan. 4, 2018

(65) Prior Publication Data
US 2019/0203720 A1    Jul. 4, 2019

(30) Foreign Application Priority Data

Jun. 29, 2016  (EP) ..................................... 16176858

(51) Int. Cl.
*F04D 7/00*    (2006.01)
*A61M 60/50*   (2021.01)
(Continued)

(52) U.S. Cl.
CPC ............. *F04D 7/00* (2013.01); *A61M 60/205* (2021.01); *A61M 60/419* (2021.01);
(Continued)

(58) Field of Classification Search
CPC .............. A61M 1/1036; A61M 1/1015; A61M 2205/3365; A61M 2205/3334
(Continued)

(56) References Cited

U.S. PATENT DOCUMENTS

2005/0267322 A1* 12/2005 LaRose ................. A61M 1/101
600/16
2013/0030240 A1   1/2013 Schima et al.
2016/0144092 A1   5/2016 Casas et al.

FOREIGN PATENT DOCUMENTS

CN          1638824 A    7/2005
CN        103328018 A    9/2013
(Continued)

OTHER PUBLICATIONS

English translation of International Search Report, issued in International Application No. PCT/EP2017/066214, dated Nov. 28, 2017, pp. 1-26, European Patent Office, Rijswijk, Netherlands.
(Continued)

*Primary Examiner* — Amanda K Hulbert
*Assistant Examiner* — Philip C Edwards
(74) *Attorney, Agent, or Firm* — Brinks Gilson & Lione

(57) ABSTRACT

Methods and apparatuses for determining operational parameters of a blood pump comprising a rotor which transports the blood are provided. The change in the behaviour of at least one first and one second operational parameter, independently from each other, of the pump, is determined. A determination of the flow through the pump and/or the difference in pressure across the pump and/or the viscosity of the blood takes into account the determined change in behaviour of the at least two operational parameters. A modelling for a dynamic model of the known quantities may be carried out and an estimation method using a Kalman filter may be used.

21 Claims, 2 Drawing Sheets

(51) Int. Cl.
*A61M 60/82* (2021.01)
*A61M 60/205* (2021.01)
*A61M 60/419* (2021.01)
*F04D 3/02* (2006.01)
*F04D 13/06* (2006.01)
*G01L 13/00* (2006.01)
*G01N 11/02* (2006.01)
*H02P 6/182* (2016.01)
*H03H 17/02* (2006.01)
*F04D 29/048* (2006.01)

(52) U.S. Cl.
CPC ............ *A61M 60/50* (2021.01); *A61M 60/82* (2021.01); *F04D 3/02* (2013.01); *F04D 13/0606* (2013.01); *G01L 13/00* (2013.01); *G01N 11/02* (2013.01); *H02P 6/182* (2013.01); *H03H 17/0202* (2013.01); *A61M 2205/3334* (2013.01); *A61M 2205/3365* (2013.01); *F04D 29/048* (2013.01); *H03H 2017/0205* (2013.01)

(58) Field of Classification Search
USPC .......................................................... 600/16
See application file for complete search history.

(56) References Cited

FOREIGN PATENT DOCUMENTS

| | | |
|---|---|---|
| EP | 0 971 212 A1 | 1/2000 |
| EP | 1 847 281 A1 | 10/2007 |
| WO | WO 03/057013 A2 | 7/2003 |
| WO | WO 2014/197541 A2 | 12/2014 |
| WO | WO 2015/195916 A1 | 12/2015 |

OTHER PUBLICATIONS

English translation of Chinese Office Action for Application No. CN 201780040840.2, dated Mar. 2, 2021, pp. 1-23.

* cited by examiner

METHOD FOR DETERMINING OPERATIONAL PARAMETERS OF A BLOOD PUMP

CROSS-REFERENCE TO RELATED APPLICATIONS

This application is a 371 nationalization of international patent application PCT/EP2017/066214 filed Jun. 29, 2017, which claims priority under 35 USC § 119 to European patent application 16 176 858.5 filed Jun. 29, 2016. The entire contents of each of the above-identified applications are hereby incorporated by reference.

TECHNICAL FIELD

The invention lies in the field of electrical engineering and can be applied particularly advantageously in medical technology.

DETAILED DESCRIPTION

Figure 1:
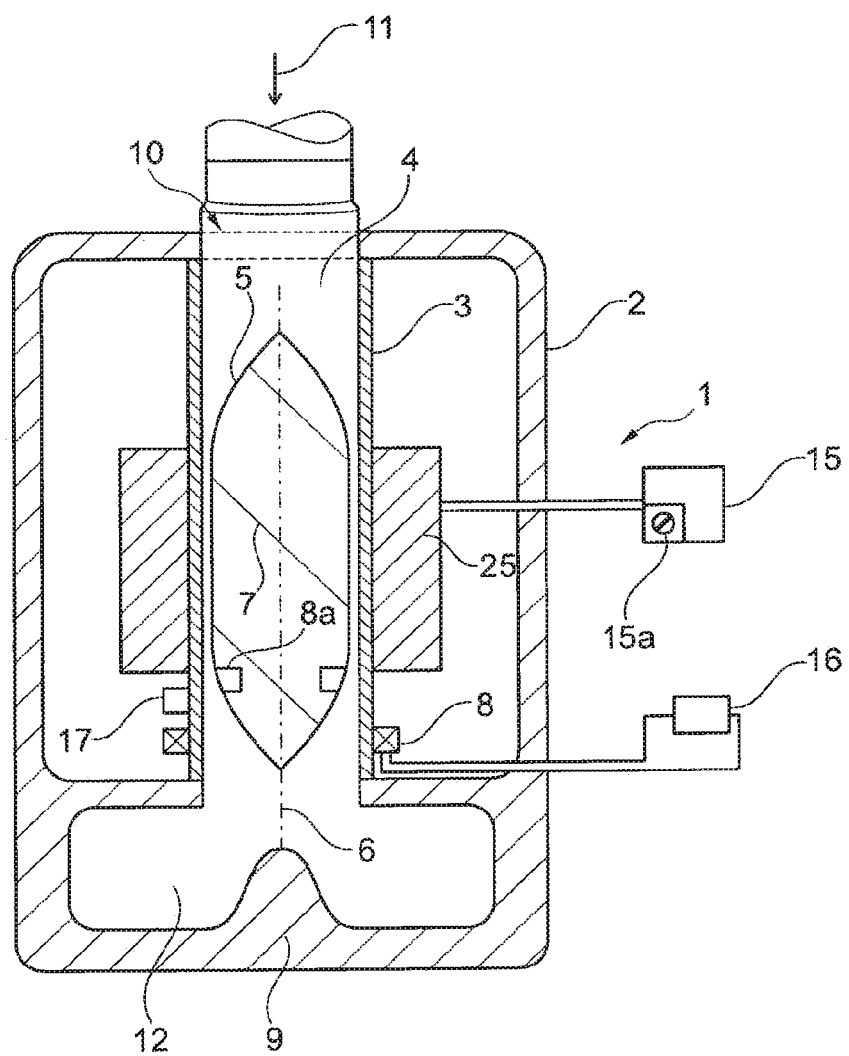
FIG. 1 schematically shows a blood pump in a longitudinal sectional view.

In recent years blood pumps, in particular heart pumps, which can be used in patients having temporary or permanent heart problems in order to support the heart or in extreme cases as a replacement for a heart that no longer functions or that is functioning poorly have been developed with increasing success. Pumps of this kind can have different operating principles. The rotor pump type, in which a rotor driven in rotation by means of a drive guides blood in the axial or radial direction within a transporting channel, is particularly widespread.

In blood pumps of this kind there is the problem of obtaining precise data regarding the generated blood flow with minimal means. Typical data sets that are of interest here are the blood flow, i.e. the volume flow rate through the pump, the pressure difference across the pump, and the blood viscosity.

These quantities specifically are usually measured in the simplest way by means of separate sensors, which are indeed available, but are costly. By contrast, operational parameters of the pump are mostly available in a relatively simple manner.

Accordingly, methods are already known from the prior art that are used to obtain information regarding the blood flow from operational parameters of a pump of this kind, which usually is electrically driven.

For example, WO 2013/003370 A2 discloses a method in which the change in the rate of the rotor rotational speed is detected and information regarding the blood flow is obtained on that basis. In particular, information regarding the pulsating, remaining cardiac output of the supported heart can be obtained in this way.

WO 2011/063994 A1 discloses a method in which a rotor of a pump is excited to perform oscillation movements so as to obtain information regarding the blood viscosity on account of an analysis by means of a model of the resonator.

Most known methods, however, are based on states described statically by characteristic curves, i.e. for example correlations of pump rotational speed, drive power of the pump, and the force acting on a rotor which guides blood in the axial direction, or similar quantities, on the precondition of a stable state. Weak points of an approach of this kind are on the one hand the fact that the blood viscosity itself can hardly be determined and has to be measured accordingly by means of separate interventions performed on the patient, and that such models do not make it possible to describe the behaviour of the pump in states of change or transition. Such states, however, are very useful in particular for obtaining information regarding a remaining cardiac function. The remaining cardiac function is naturally pulsating and thus leads to rapid changes in the physical load on the pump.

Against the background of the prior art, the object of the present invention is to create a method for determining operational parameters of a blood pump that can also be used when operational parameters are changing continuously.

Accordingly, the invention relates to a method for determining, in particular for estimating, operational parameters of a blood pump comprising a rotor which transports the blood, wherein the change in the behaviour of at least one first and one second operational parameter of the pump, which are independent from each other, is determined and wherein a determination of the flow through the pump and/or the difference in pressure across the pump and/or the viscosity of the blood takes into account the determined change in behaviour of the at least two operational parameters.

Since rate changes over time can also be detected or determined continuously for at least two detectable operational parameters, in contrast to the prior art a dynamic model which uses interlinked independent differential equations which each describe dynamic dependencies of a number of pump parameters can be selected for the model-like description of a blood pump. A model of this kind thus can be applied for dynamic states, i.e. states of transition or change of the pump. The rate changes over time of the detected operational parameters can be either measured directly or, via continuous detection of the operational parameters themselves, can be mathematically determined by calculating the difference. To this end, appropriate scanning rates shall be selected. Examples of potential description models will be specified further below.

For example, it can be provided that at least the rotational speed of the pump is measured as first operational parameter and a change in rate of the rotational speed over time is determined.

In addition, a second time derivative of the rotational speed can also be determined and taken into consideration. For example, apart from the moment of inertia of the rotor, the viscosity of the blood also has an influence on the acceleration values of the rotor, and therefore a corresponding model can contribute to the determination of the blood viscosity.

It can additionally be provided that in a pump a quantity that represents a force acting on the rotor in the axial direction, in particular an axial deflection of the rotor in a magnetic axial bearing, is measured as second operational parameter, and in that a change in behaviour of this quantity over time is determined.

Pump rotors that transport blood in the axial direction or in the axial/radial direction are often mounted in magnetic bearings, such that in the case of a magnetic bearing it is possible to determine the axial force acting on the rotor directly on the basis of the axial deflection of the rotor. In the case of an actively controlled magnetic bearing (for example zero-force control), the axial force acting on the rotor can be determined by the bearing position and the bearing current strength. The bearing position in the axial direction shows a clear correlation with the back EMF (electromagnetic force) of a drive motor when this is directly integrated in the rotor, for example by making the rotor shaft of the pump rotor identical to the shaft of the drive motor. An axial deflection, under otherwise identical conditions, increases or reduces the back EMF. In the case of passive bearings, however, the axial bearing position can also be measured by a position sensor, for example a Hall sensor. Acceleration values of a rotor in the axial direction, apart from being dependent on the mass of the rotor, are also dependent on the viscosity of the blood and dynamic quantities of the blood flow, such that these acceleration values also produce a correlation with the blood viscosity.

The rate of change of the axial deflection of the rotor in the further sense can also be determined by analysis of the oscillation behaviour of the rotor in the axial direction.

To this end, various methods are known, for example measurement of the natural frequency of the rotor relative to the oscillation in the axial direction following interference/excitation, or determination of the achievable oscillation amplitude in the event of a forced oscillation with a specific power input.

It can additionally be provided that besides the first and second operational parameter and their change in behaviour, a drive power of the rotor, in particular by means of a drive motor current strength and in particular additionally the current strength through the bearing coil of a magnetic bearing, in particular an axial magnetic bearing, is measured and is taken into consideration in the determination. If the drive power of the rotor, in particular determined on the basis of the drive motor current strength, the rotational speed and a quantity representing the force acting on the rotor in the axial direction are thus measured and time derivatives of the kind explained above are likewise detected or determined, differential equations coupled with one another which produce a correlation between these quantities can thus be solved at least approximately. To this end, numerical approximation methods can be used, for example.

The use of estimation methods with systematic consideration of measurement uncertainties and disturbance factors appears to be more advantageous. This means that, for the use of an estimation method of this kind (also referred to as a state observer), disturbance factors can be determined in order to achieve a successful estimation as efficiently as possible. Such disturbance factors can be for example determined by sample measurements or defined by parameterisation. In the event of a parameterisation, for example a parameter set can be selected, the estimation performed, and the quantities to be estimated (pump flow, viscosity and difference in pressure across the pump, for example performed with temporarily used, accurately measuring sensors) are determined using a real measurement.

For example, it has proven to be expedient if the two differential equations coupled with one another $$J\frac{d\omega}{dt} = KI_m - B\omega - f_T(\omega, Q) \text{ and}$$

$$m\frac{d^2x}{d^2t} + \mu\frac{dx}{dt} = Ki I_b + kx - f_x(\omega, Q, H)$$

are taken into consideration in the determination. Here, J is the moment of inertia of the rotor, w is the angular velocity of the rotor, $I_m$ is the motor current strength, K is a torque constant, B is a friction constant, and $f_T$ is the load moment of the rotor, which is dependent on the rotational speed and the blood flow Q. m denotes the mass of the rotor, x is the axial deflection of the rotor in the bearing, µ is a friction constant, Ki is the current rigidity, $I_b$ is the bearing current strength of an actively controlled magnetic bearing, kx is the passive magnetic force of the magnetic bearing, and $f_x$ a force that acts axially on the rotor and is dependent on the rotational speed, the pump flow and the difference in pressure H across the pump.

Additionally and in order to improve the estimate, it can also be provided that the differential equation $$L\frac{dQ}{dt} = -H + f_Q(\omega, Q)$$

is additionally taken into consideration. This differential equation describes the dependency of the change over time of the pump flow dQ/dt on the rotational speed ω, the difference in pressure across the pump H, and a quantity $f_Q$ dependent on the rotational speed ω and the pump flow. $f_Q$ is a flow resistance of the pump dependent on the pump flow and/or the rotational speed.

At least one constant, but in most cases a plurality of the constants from the three described differential equations is/are dependent on the viscosity. The functions $f_T$, $f_x$ and $f_Q$ can be dependent on the viscosity.

Additionally or instead of the last-mentioned differential equation, it can also be provided that a back EMF (electromagnetic feedback) of a brushless motor of the rotor is measured and a differential equation is taken into consideration, which describes the dependency of the back EMF on the rotor deflection in the axial direction, the rotational speed and the drive power.

The voltage function at a motor stator can be described as follows:

$$V = RI + L\frac{dI}{dt} + f(\omega, x)$$

f(ω,x) is the back EMF, R and L are the resistance and the inductance of the coil, and I is the induced current in this coil.

It has proven to be particularly advantageous if the flow through the pump and/or the difference in pressure across the pump and/or the viscosity of the blood as solution of the differential equations are/is determined by an estimation method, in particular with use of a Kalman filter. What is known as a Kalman filter, in particular an extended or unscented Kalman filter, describes a method for estimating solutions, for example of the described dynamic models under consideration of disturbance factors. Kalman filters of this kind are available as finished software modules and can be suitably parameterised for corresponding applications. Disturbance factors can also be characterised, that is to say either are likewise parameterised to the best of knowledge or are determined by sample measurements with controllable disturbances. After setting up a Kalman filter in this way, the module can be supplied with the continuously detected operational parameters by inputting these or transmitting them electronically, and the filter then outputs estimation values for the solution of the differential equations in the form of estimation values for the flow of the pump and/or the difference in pressure across the pump and/or the viscosity of the pumped blood.

Further methods that can be used in this context to determine the unknown states in a blood pump are recurrent neuronal networks or neuro-fuzzy systems.

Since the described method is particularly successful in the description of dynamic models for a blood pump, it can also be provided that the electric drive power of the rotor and/or a bearing position of the rotor are changed selectively in order to attain a dynamic reaction of the pump. Since the magnitude of the changes as a result of the selective modifications during operation differ from zero, the method according to the invention can fully implement its advantages in a process of this kind and can successfully determine the operational parameters to be estimated.

It can also be provided that the dynamic, in particular cyclic changes in the blood flow and/or the operational parameters of the pump occurring as a result of the pulsatility and/or remaining cardiac activity of a patient's heart are determined in order to detect a change in behaviour over time of a first and second operational parameter during a dynamic reaction of the pump. In this case, the method according to the invention makes use of the cyclic changes provided anyway during operation in the case of a living patient with remaining cardiac function so as to utilise the advantages thereof in the description of dynamic pump situations. If, for example, the cyclic changes of the operational parameters provided in the described way are too small, they can be amplified by with the cyclic changes of the aforementioned operational parameters of the pump so as to generate a dynamic favourable to the model application. Depending on the extent of the changes, the electric drive power of the rotor and/or a bearing position of the rotor can be modified selectively so as to be able to detect a meaningful dynamic behaviour of the pump.

The invention also relates to a method for determining, in particular for estimating, operational parameters of a blood pump comprising a rotor which transports the blood, in which method operational parameters of the pump are detected continuously, wherein at least the back EMF (electromagnetic force) of a brushless drive motor of the rotor, the rotor deflection in the axial direction, the rotor rotational speed and the drive power are detected, the quantities are linked with one another on the basis of a differential equation, and the difference in pressure across the pump and/or the flow through the pump and/or the viscosity of the blood are/is determined by means of an estimation method with use of a Kalman filter.

Here, the first-mentioned differential equation can also be linked with the differential equation $$J\frac{d\omega}{dt} = KI_m - B\omega - f_T(\omega, Q).$$

The invention also relates to a method for determining, in particular for estimating, the difference in pressure over a blood pump comprising a rotor which transports the blood, in which method operational parameters of the pump are detected continuously, wherein at least the back EMF of a brushless drive motor of the rotor, the rotor deflection in the axial direction or a bearing current representative of this, the rotor rotational speed and the drive power are detected, the quantities are linked with one another on the basis of a differential equation, and the difference in pressure is determined by means of an estimation method with use of a Kalman filter.

The invention further relates to a method for determining, in particular for estimating, the flow through a blood pump comprising a rotor which transports the blood, in which method operational parameters of the pump are detected continuously, wherein at least the back EMF of a brushless drive motor of the rotor, the rotor deflection in the axial direction or a bearing current representative of this, the rotor rotational speed and the drive power are detected, the quantities are linked with one another on the basis of a differential equation, and the flow is determined by means of an estimation method with use of a Kalman filter.

The invention further also relates to a method for determining, in particular for estimating, the blood viscosity with use of a blood pump comprising a rotor which transports the blood, in which method operational parameters of the pump are detected continuously, wherein at least the back EMF of a brushless drive motor of the rotor, the rotor deflection in the axial direction or a bearing current representative of this, the rotor rotational speed and the drive power are detected, the quantities are linked with one another on the basis of a differential equation, and the blood viscosity is determined by means of an estimation method with use of a Kalman filter.

Disturbances in the determination of the values of the stated quantities or their influences on the consistency of the determination can thus be minimised by the use of estimation methods.

A further method according to the invention can provide that the change in behaviour of the flow through the pumps is detected or determined, and in that the difference in pressure across the pump and/or the blood viscosity are/is estimated by means of an estimation method.

It can also be provided that the change in behaviour of a pressure measured at the pump, in particular at the pump inlet, is detected or determined, and in that for example the difference in pressure across the pump is estimated by means of an estimation method and the flow through the pump and/or the viscosity of the blood are/is estimated on the basis of this estimation.

An estimation without the detection of operational parameters of a magnetic or non-magnetic bearing is thus also possible.

Here, it can be provided that the method is used in a pump with exclusively mechanical, in particular non-magnetic bearing of the pump rotor.

In an estimation method of this kind it can additionally be provided that the differential equation $$J\frac{d\omega}{dt} = KI_m - B\omega - T(\omega, Q)$$

is taken into consideration in the determination.

In addition it can be provided that the differential equation $$L\frac{dQ}{dt} = a\omega^2 - H - f_Q(\omega, Q)$$

is additionally taken into consideration.

For the use of the method in accordance with the last-mentioned method variant without access to operational parameters of an axial bearing, that is to say without detection of the thrust of the rotor in the axial direction, a blood pump device comprising a blood pump can be provided, comprising a rotor which transports the blood at least partially in the axial direction and which is mounted in a non-magnetic axial bearing, comprising a device for detecting the rotational speed of the rotor as first operational parameter and comprising a device for detecting the flow through the pump or a pressure at the pump inlet as second operational parameter, and comprising a device for determining the change in behaviour over time of the rotational speed and the flow or the pressure, and comprising a determination device which is designed to determine the flow through the pump and/or the difference in pressure across the pump and/or the viscosity of the blood under consideration of the determined change in behaviour of the at least two operational parameters.

Effective estimation methods are thus made possible, even without use of bearing operational parameters.

The invention, besides a method of the type mentioned and explained above, also relates to a blood pump device comprising a blood pump comprising a rotor which transports the blood and which is mounted in a magnetic axial bearing, comprising a device for detecting the rotational speed of the rotor as first operational parameter and comprising a device for detecting a rotor position in the axial direction as second operational parameter, and comprising a device for determining the change in behaviour over time of the rotational speed and the rotor position, and comprising a determination device which is designed to determine the flow through the pump and/or the difference in pressure across the pump and/or the viscosity of the blood under consideration of the determined change in behaviour of the at least two operational parameters. Amongst others, blood pumps that can be used here are those that transport the blood at least partially in the axial direction.

The determination device can comprise for example a data processing device, for example a microcontroller, which feeds detected operational parameters and their values of change either to a Kalman filter or itself contains a program module which performs the function of a Kalman filter.

To this end, a device for detecting the drive power of the rotor, in particular by the detection of a drive motor current strength and in particular comprising a device for detecting the bearing current strength of an axial magnetic bearing or the axial deflection of a rotor in a passive magnetic bearing, can additionally be provided. Likewise, a device for measuring the back EMF and in particular also for determining the rate of change thereof over time can be provided. A device for measuring the pressure at the inlet of the blood pump or for measuring the volume flow rate through the blood pump, in particular with corresponding sensors for the pressure measurement and/or the measurement of the flow, can also be provided.

Figure 2:
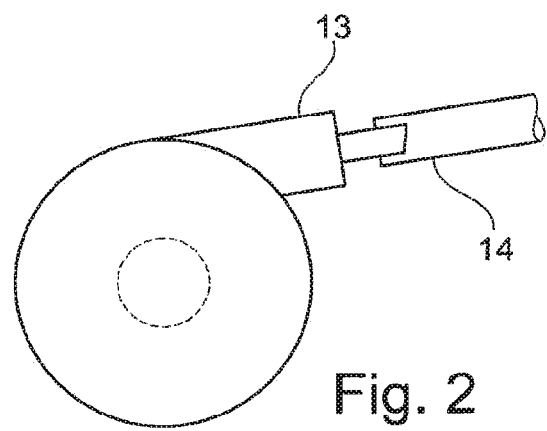
FIG. 2 shows the blood pump from FIG. 1 in a front view.
Figure 3:
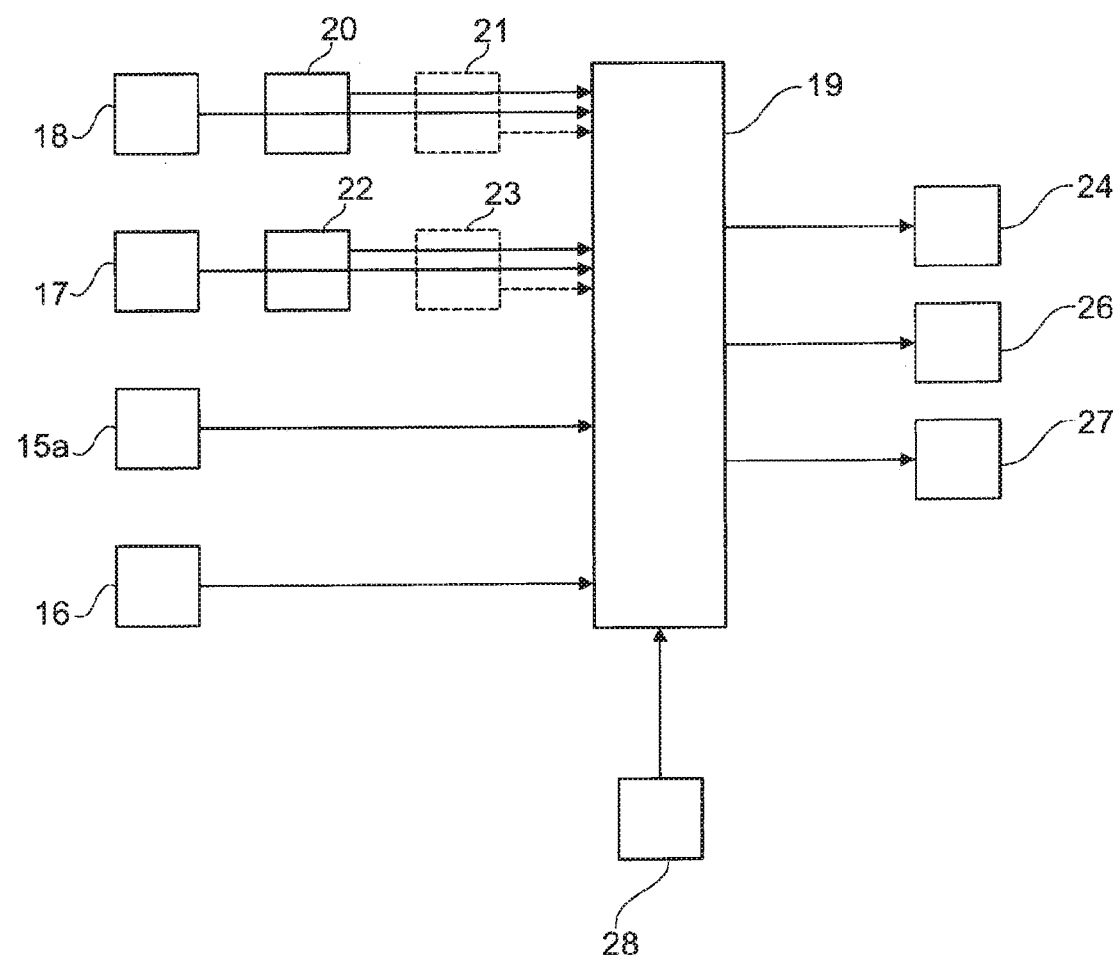
FIG. 3 schematically shows a device for carrying out the method according to the invention.

The invention will be presented and explained hereinafter on the basis of exemplary embodiments in figures of a drawing, in which FIG. 1 schematically shows a blood pump in a longitudinal sectional view, FIG. 2 shows the blood pump from FIG. 1 in a front view, and FIG. 3 schematically shows a device for carrying out the method according to the invention.

FIG. 1 schematically shows a blood pump 1 comprising a pump housing 2, in which there is disposed a pump tube 3. A rotor 5 is mounted in the pump tube 3 so as to be driveable in rotation and comprises a delivery element in the form of a rib 7 running circumferentially around the rotor 5 in a helical manner. The rotor 5 rotates, when it is driven, about the axis of rotation 6. At the end 4 of the tube, at the pump inlet, blood is hereby sucked through a cannula connected there for example, in the direction of the arrow 11. The cannula is denoted by 10 and is inserted into the pump tube 3 or docked thereon.

Permanent magnets (not shown in greater detail) are arranged within the rotor 5, in such a way that the rotor 5 forms the rotor of a brushless electric motor. The drive of the motor is provided by means of suitable control of windings of the external stator 25. This can be activated for example by pulse wave modulated signals. The control device is denoted by 15 and comprises a device 15a for detecting the drive current for the rotor 5.

The rotor can be mounted in the pump tube radially by means of radial magnetic bearings, which are not shown in greater detail. A region can also be provided in which the rotor forms a hydrodynamic radial bearing, jointly with the pump tube.

In the axial direction the rotor is mounted in one variant of the invention by means of a magnetic axial bearing 8, which interacts with a magnetic assembly in the rotor, in particular with a magnetic ring 8a. The magnetic bearing 8 (more precisely: the stationary part thereof) is acted on with a bearing current by means of a bearing control 16, in such a way that the position of the rotor 5 in the axial direction 6 is controlled into the zero-force position. For this purpose, a sensor is provided for detecting the axial position of the rotor 5 and is denoted by 17.

Within the scope of the invention, however, a pump comprising exclusively non-magnetic, mechanical bearings, in particular plain bearings, more particularly hydrodynamic bearings, can be provided.

The rotor 5 transports the blood through the pump tube 3 into the outlet space 12, where the blood flows radially outwardly to a pump outlet 13, which is visible in FIG. 2. The blood flows from the pump outlet 13 into a cannula 14 connected to the pump outlet.

In the configuration explained above, the rotational speed of the rotor 5 can be detected by the control device 15. With an appropriate sampling rate, the rate of change, i.e. the first derivative of the rotational speed over time, can be determined with sufficient accuracy, as can also the second derivative of the rotational speed over time as appropriate. The motor current can also be detected by the control device in the form of the current strength, which for example can be integrated via the pulse wave modulated signals. The axial deflection of the rotor 5 can be determined by means of the Hall sensor 17; with an appropriate sampling rate the time derivative $\Delta x/\Delta t$ of this quantity and the second time derivative of this quantity can also be determined. Alternatively or additionally, the bearing current through the controlled axial bearing 8 can be determined as representative quantity for an axial force acting on the rotor instead of the axial deflection in the control device 16 for the bearing current.

All required physical quantities which form quantity operational parameters of the pump, are thus available directly at the pump.

The parameters of pump flow (conveyed liquid volume per unit of time), difference in pressure across the pump (difference in the pressures at the pump inlet 4 on the one hand and at the pump outlet 13 on the other hand) and blood viscosity can be determined continuously by the method according to the invention on the basis of the detected operational parameters by estimation, that is to say also very quickly or without time offset.

For some variants of the invention, a pressure sensor can also be provided at the pump inlet. In addition, a flow sensor can also be provided in, before or after the pump.

This will be explained schematically with reference to FIG. 3. In FIG. 3 the rotational speed sensor is denoted by 18. The value of the detected rotational speed is conducted to the processing device 19. Here, the rotational speed value passes to the device 20 for determining the rate of change of the rotational speed (time derivative). From here, the momentary value of the rate of change is forwarded to the processing device 19. A device 21 for determining the second derivative of rotational speed over time potentially also obtains the corresponding measured value of the rotational speed and can determine the second derivative and, if required, forward it to the processing device 19.

The sensor for the axial deflection of the rotor is denoted by 17 and transfers the momentarily detected value of the deflection to the processing device 19. The corresponding value is also transferred to the processing device 22, which determines the first time derivative of the axial deflection of the rotor and transfers this to the processing device 19. Potentially the momentary value of the axial deflection can also be transferred to the processing device 23, which determines the second time derivative of the axial deflection and forwards it to the processing device 19. Instead of the axial deflection, this configuration can also be applied for a bearing current strength.

The sensor 15a determines in each case the drive motor current strength or a value representative for same and transfers this to the processing device 19.

The control device 16 potentially transfers the value of the bearing current strength through the actively controlled axial magnetic bearing 8 to the processing device 19.

The processing device 19 comprises an estimation module, which with the aid of a Kalman filter or an extended Kalman filter continuously determines estimations of the quantities constituted by the flow rate of the pump, difference in pressure across the pump and blood viscosity. The three quantities are shown in the displays 24, 26 and 27 and, if expedient or necessary, are stored and/or forwarded to a further data processing device. A continuous monitoring of the estimated quantities for overshooting or undershooting of thresholds with alarm triggering can also be provided. In addition to the determined operational parameters, as further input quantities the processing device 19 processes the parameters delivered by the parameterisation module 28 representing the influence of disturbance factors and measurement inaccuracies on the estimation process. A reliable estimation of the stated quantities is thus possible with use of the Kalman filter.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A method for determining operational parameters of a blood pump comprising a rotor which transports blood, the method comprising:
   determining a change in behaviour of at least two operational parameters including a first operation parameter and a second operation parameter, independently from each other, of the blood pump; and
   determining a flow through the blood pump, a difference in pressure across the blood pump, and/or a viscosity of the blood based on the determined change in behaviour of the at least two operational parameters,
   wherein in the blood pump with the rotor which transports the blood, a quantity that represents a force acting on the rotor in an axial direction of the blood pump is measured as the second operational parameter, and a change in behaviour of this quantity over time is determined.

2. The method of claim 1, wherein at least a rotational speed of the blood pump is measured as the first operational parameter and a change in rate of the rotational speed over time is determined as the change in behaviour of the second operational parameter.

3. The method of claim 1, wherein determining the change in behaviour of the second operational parameter comprises determining a first time derivative of the second operational parameter.

4. The method of claim 1, wherein besides the first and second operational parameters and their change in behaviour, a drive power of the rotor is measured and is taken into consideration in the determination of the flow through the blood pump, the difference in pressure across the blood pump, and/or the viscosity of the blood.

5. The method of claim 1, wherein electric drive power of the rotor and/or a bearing position of the rotor are changed selectively in order to attain a dynamic reaction of the blood pump.

6. The method of claim 1, wherein the change in behaviour of the flow through the blood pump is detected or determined, and wherein the difference in pressure across the blood pump and/or the blood viscosity are/is estimated.

7. The method of claim 6, wherein the blood pump rotor has an exclusively mechanical, non-magnetic bearing.

8. The method of claim 6, wherein differential equation $$J\frac{d\omega}{dt} = KI_m - B\omega - T(\omega, Q)$$

is taken into consideration in the determination of the blood viscosity.

9. The method of claim 8, wherein differential equation $$L\frac{dQ}{dt} = a\omega^2 - H - f_Q(\omega, Q)$$

is additionally taken into consideration in the determination of the blood viscosity.

10. A method for determining operational parameters of a blood pump comprising a rotor which transports blood, the method comprising:

detecting operational parameters of the blood pump continuously;
determining a change in behaviour of at least two operational parameters including a first operation parameter and a second operation parameter, independently from each other, of the blood pump; and
determining a flow through the blood pump, a difference in pressure across the blood pump, and/or a viscosity of the blood based on the determined change in behaviour of the at least two operational parameters,
wherein two differential equations coupled with one another $$J\frac{d\omega}{dt} = KI_m - B\omega - T(\omega, Q) \text{ and}$$

$$m\frac{d^2x}{d^2t} + \mu\frac{dx}{dt} = KiI_b + kx - f_x(\omega, Q, H)$$

are taken into consideration in the determination of the flow through the blood pump, the difference in pressure across the blood pump, and/or the viscosity of the blood.

11. The method of claim 10, wherein differential equation $$L\frac{dQ}{dt} = a\omega^2 - H - f_Q(\omega, Q)$$

is additionally taken into consideration in the determination of the flow through the blood pump, the difference in pressure across the blood pump, and/or the viscosity of the blood.

12. The method of claim 10, wherein a back EMF of a brushless drive motor of the rotor is measured and a differential equation is taken into consideration which describes a dependency of the back EMF on a rotor deflection in an axial direction of the blood pump, a rotational speed of the rotor, and drive power.

13. The method of claim 10, wherein the flow through the blood pump, the difference in pressure across the blood pump, and/or the viscosity of the blood as a solution of the differential equations are/is determined by estimating with a Kalman filter.

14. A method for determining operational parameters of a blood pump comprising a rotor which transports blood, the method comprising:
   determining a change in behaviour of at least two operational parameters including a first operation parameter and a second operation parameter, independently from each other, of the blood pump; and
   determining a flow through the blood pump, a difference in pressure across the blood pump, and/or a viscosity of the blood based on the determined change in behaviour of the at least two operational parameters,
   wherein dynamic changes in the blood flow, the operational parameters of the blood pump occurring as a result of pulsatility, and/or remaining cardiac activity of a patient's heart are determined in order to detect a change in behaviour over time of the first and the second operational parameters during a dynamic reaction of the blood pump.

15. A method for determining operational parameters of a blood pump comprising a rotor which transports blood, the method comprising:
   detecting operational parameters of the blood pump continuously;
   detecting at least a back EMF (electromagnetic force) of a brushless drive motor of the rotor, a rotor deflection in an axial direction of the blood pump or a bearing current representative of the rotor deflection in the axial direction, a rotor rotational speed, and a drive power;
   linking the detected quantities with one another based on a differential equation; and
   determining a difference in pressure across the blood pump, a flow through the blood pump, and/or a viscosity of the blood as an estimate using a Kalman filter.

16. A method for determining a difference in pressure across a blood pump comprising a rotor which transports blood, the method comprising:
   detecting operational parameters of the blood pump continuously, wherein at least back EMF of a brushless drive motor of the rotor, a rotor deflection in an axial direction of the blood pump or a bearing current representative of the rotor deflection in the axial direction, a rotor rotational speed, and drive power;
   linking the detected quantities with one another based on a differential equation; and
   determining the difference in pressure by estimating with a Kalman filter.

17. A method for determining a flow of blood through a blood pump comprising a rotor, the method comprising:
   detecting, continuously, operational parameters of the blood pump;
   detecting at least a back EMF of a brushless drive motor of the rotor, a rotor deflection in an axial direction of the blood pump or a bearing current representative of the rotor deflection in the axial direction, a rotor rotational speed, and drive power;
   linking the detected quantities with one another based on a differential equation; and
   determining the flow of blood as an estimate based on a Kalman filter.

18. A method for determining a blood viscosity with use of a blood pump comprising a rotor which transports blood, the method comprising:
   detecting operational parameters of the blood pump continuously;
   detecting at least back EMF of a brushless drive motor of the rotor, a rotor deflection in an axial direction of the blood pump or a bearing current indicative of the rotor deflection in the axial direction, a rotor rotational speed, and a drive power;
   linking the detected quantities with one another based on a differential equation; and
   determining the blood viscosity as an estimate by application of a Kalman filter.

19. A method for determining operational parameters of a blood pump comprising a rotor which transports blood, the method comprising:
   detecting operational parameters of the blood pump continuously;
   determining a change in behaviour of at least two operational parameters including a first operation parameter and a second operation parameter, independently from each other, of the blood pump; and
   determining a flow through the blood pump, a difference in pressure across the blood pump, and/or a viscosity of the blood based on the determined change in behaviour of the at least two operational parameters,
   wherein the change in behaviour of a pressure measured at a blood pump inlet is detected or determined, and wherein the difference in pressure across the blood pump, the flow through the blood pump, and/or the viscosity of the blood are/is estimated.

20. A blood pump device comprising a blood pump comprising:
    a rotor configured to transport blood at least partially in an axial direction of the blood pump, the rotor mounted in a magnetic axial bearing;
    a device for detecting a rotational speed of the rotor as a first operational parameter;
    a device for detecting a rotor position in an axial direction of the blood pump as a second operational parameter;
    a device for determining a change in behaviour over time of the rotational speed and the rotor position;
    a determination device configured to determine a flow through the blood pump, a difference in pressure across the blood pump, and/or a viscosity of blood based on the determined change in behaviour of the first and second operational parameters; and
    a device for detecting the drive power of the rotor by the detection of a drive motor current strength, and a device for detecting the bearing current strength of an axial magnetic bearing.

21. The blood pump device of claim 20, wherein the determination device is configured to determine the flow through the blood pump, the difference in pressure across the blood pump, and/or the viscosity of the blood by an estimation with a Kalman filter.

* * * * *